United States Patent [19]

Skov et al.

[11] Patent Number: 4,520,216
[45] Date of Patent: May 28, 1985

[54] PROCESS FOR THE PREPARATION OF SYNTHETIC HYDROCARBONS

[75] Inventors: Allan Skov, Lyngby; Jens R. Rostrup-Nielsen, Virum, both of Denmark

[73] Assignee: Haldor Topsoe, Lyngby, Denmark

[21] Appl. No.: 609,045

[22] Filed: May 10, 1984

[30] Foreign Application Priority Data

May 11, 1983 [DK] Denmark ............... 2105/83

[51] Int. Cl.$^3$ .............................. C07C 1/20
[52] U.S. Cl. ................... 585/315; 585/322; 585/327; 585/408; 585/469; 585/640; 585/733
[58] Field of Search ............ 585/315, 314, 322, 327, 585/408, 469, 733, 640, 25 M

[56] References Cited

U.S. PATENT DOCUMENTS

| | | | |
|---|---|---|---|
| 4,044,061 | 8/1977 | Chang et al. | 585/469 |
| 4,058,576 | 11/1977 | Chang et al. | 585/469 |
| 4,100,219 | 7/1978 | Rodewald | 585/469 |
| 4,159,995 | 7/1979 | Haag et al. | 585/408 |
| 4,197,418 | 4/1980 | Lee et al. | 585/408 |
| 4,418,236 | 11/1983 | Cornelius | 585/408 |

Primary Examiner—Delbert E. Gantz
Assistant Examiner—A. Pal
Attorney, Agent, or Firm—Lawrence Rosen

[57] ABSTRACT

Synthetic hydrocarbons, especially high octane gasoline, are prepared by catalytic conversion in two steps of a synthetic gas containing hydrogen and carbon oxides. In the first step the synthesis gas is converted at 10–80 bar and 200°–300° C. into an intermediate containing methanol and/or dimethyl ether. Useful catalysts for methanol synthesis are oxides of chromium, aluminium and/or copper, and zinc; and for dimethyl ether synthesis certain zeolites. In the second step the entire intermediate from the first step is converted at the same pressure as in the first step and an inlet temperature of 300°–340° C. while supplying heat to obtain an outlet temperature of 410°–440° C.; the difference between inlet and outlet temperature being at least 30° C. higher than the temperature increase caused by the conversion reaction. As catalyst in the second step one can use any conventional catalyst for converting methanol and/or dimethyl ether into hydrocarbons, especially synthetic zeolites. The raw product stream from the second step is cooled and thereby separated into a condensed hydrocarbon product stream and a gaseous recycle stream, the latter being recycled without further separation to the inlet of the first stream and here combined with fresh synthesis gas feed. There is obtained a low rate of deactivation of the catalyst used in the second step and a high quality hydrocarbon product.

3 Claims, 1 Drawing Figure

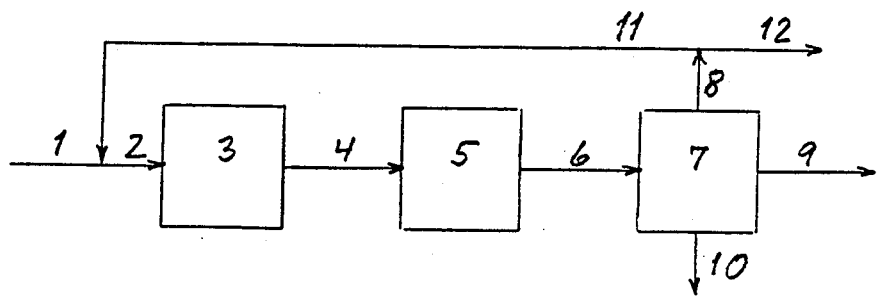

4,520,216

PROCESS FOR THE PREPARATION OF SYNTHETIC HYDROCARBONS

FIELD OF THE INVENTION

The present invention relates to the preparation of synthetic hydrocarbons by catalytic conversion in two steps of a synthesis gas containing hydrogen and carbon oxides.

The invention especially relates to the preparation of synthetic high octane gasoline.

BACKGROUND OF THE INVENTION

There has already been described, i.a. in the patent literature, a large number of processes for preparing various petroleum fractions from various fossil fuels.

According to one of these processes hydrocarbon mixtures, including high octane gasoline, are prepared directly from lower alcohols and/or corresponding ethers by the catalytic reaction over synthetic zeolite catalysts. The process and the catalysts are described, i.a., in the U.S. Pat. Nos. 3,702,886, 3,709,979, 3,832,449, 3,899,544, and 3,911,041. The alcohols and/or ethers usable as starting materials may have been prepared in separate plants. It has been found advantageous, however, to integrate the process for the preparation of hydrocarbons by means of zeolite catalysts with a process for preparing the said alcohols and/or ethers from a suitable raw material such as natural gas or coal. Such integrated processes have already been described and especially two of them have been the subject of interest. In one of them a synthesis gas containing hydrogen and carbon oxides is converted via methanol (MeOH) into hydrocarbons, and in the other the conversion into hydrocarbons takes place via methanol/dimethyl ether (MeOH/DME).

Such a process for conversion via MeOH is described, e.g. in German Patent Publication DE-OS No. 2,846,693. In the process according to the German Patent Publication a gas mixture mainly consisting of carbon oxides and hydrogen is reacted in a first step using a methanol synthesis catalyst to produce an intermediate product containing methanol. The entire intermediate product is then further converted in a second step using a zeolite catalyst to produce a product stream containing hydrocarbons. The product stream is cooled and a fraction of the stream consisting of hydrocarbons containing at least 5 C-atoms per molecule is separated while the remaining part of the product stream is recycled to the inlet of the first step. The second step of the process preferably is carried out in a cooled reactor at a temperature of 250°–400° C.

A process for conversion via MeOH/DME is described e.g. in U.S. Pat. No. 3,894,102. In the process according to that specification a mixture of carbon monoxide and hydrogen is contacted with a catalyst mixture consisting of a methanol synthesis catalyst and an acidic dehydration catalyst in a first step to produce an intermediate product having a high content of DME. The intermediate product or a part thereof is thereafter reacted in a second step over a zeolite catalyst to produce a product containing high octane gasoline.

Irrespective of which of the described known process routes is employed it has in practice not been possible to carry out the zeolite catalyzed process step without process-related problems as described below.

The preparation of hydrocarbons by the conversion of MeOH and/or DME takes place by exothermal reactions and is conducted using controlled temperature conditions. Thus, according to the known technique the temperature is controlled by using cooled reactors or by using one or more adiabatic reactors optionally combined with recycling of a fraction of the product gas to limit the adiabatic temperature increase.

It is important to control the temperature considering the catalyst as well as the composition of the product obtained.

Thus, using a relatively low temperature results in a slow deactivation of the catalyst but at the same time a product of poor quality is obtained (high content of undesirable components, especially durene).

On the other hand a relatively high temperature results in a fast deactivation of the catalyst but at the same time a product of good quality is obtained.

The deactivation is caused by the formation of high molecular weight compounds and possibly carbon which is deposited on the surface and in the pore system of the catalyst, thereby blocking the active centers of the catalyst resulting in reduced catalytic activity.

Hitherto it has not been possible to obtain at the same time a slow deactivation and the desired product composition. Therefore it has been necessary to carry out (1) frequent regeneration/replacement of the catalyst or
(2) further treatment of the product to obtain an end product of the desired composition.

BRIEF DESCRIPTION OF THE INVENTION

Surprisingly, it has now been found that by the process according to the invention it is possible to achieve a low deactivation rate for the zeolite catalyst and simultaneously, without a complicated fractionation to obtain a product of the desired composition.

Thus, the invention relates to a process for the preparation of synthetic hydrocarbons, especially synthetic high octane gasoline, by catalytic conversion in two steps of a synthesis gas containing hydrogen and carbon oxides, whereby in the first step a feed steam containing the synthesis gas is converted in the presence of a catalyst, at a pressure of 10–80 bar, preferably 30–60 bar, and at a temperature of 200°–300° C., preferably 240°–270° C., into an intermediate product containing methanol and/or dimethyl ether, after which in the second step the entire intermediate product from the first step is converted, in the presence of a catalyst and at substantially the same pressure as in the first step, to form a raw product stream of hydrocarbons, which raw product stream is cooled and thereby separated into a condensed product stream and a gaseous recycle stream, which recycle stream without further separation is recycled to the inlet of the first step. The process is characterized in carrying out the second step at an inlet temperature of 300°–340° C., preferably 320°–330° C., while supplying heat to obtain an outlet temperature of 410°–440° C., preferably 420°–430° C., the difference between inlet temperature and outlet temperature being at the same time at least 30° C. higher than the temperature increase caused by the heat generated by the chemical reaction, taking place in the second step.

DESCRIPTION OF THE DRAWING

The drawing shows schematically a flow sheet embodying the process of the invention. A stream 1 of a synthesis gas contaning hydrogen and carbon oxides is combined with a recycle stream 11 to form a feed stream 2 which is passed to a cooled reactor 3 in which the first conversion step is carried out to form the intermediate product containing methanol and/or dimethyl ether. A stream 4 of this intermediate product is passed to a reactor 5 in which the second conversion step is carried out to convert the intermediate product into a raw product stream 6 contaning hydrocarbons. Reactor 5 may be heated by conventional means such as electrical heating means. Raw product stram is passed to a separator 7 where it is cooled, e.g. to a temperature of 15° C. The cooling causes the raw product to be separated and from separator 7 there is removed two streams, viz. a side stream 10 mainly consisting of water, a product stream 9 and a side stream 8. The side stream 8 is divided into two streams of identical composition, viz. recycle stream 11 to be combined with feed stream 1, and a side stream 12 (purge) which is discarded. Recycle stream 11 comprises the main part of side stream 8.

DETAILED DESCRIPTION OF THE INVENTION

As mentioned, the intermediate product may contain methanol (MeOH) or dimethyl ether (DME) or both MeOH and DME. Which of these process routes to follow depends on a number of factors.

The conversion of carbon oxides and hydrogen in the first step with formation of MeOH as the essential intermediate product proceeds according to the reactions $$CO + 2H_2 \rightleftharpoons CH_3OH \qquad (1)$$

$$CO + H_2O \rightleftharpoons CO_2 + H_2 \qquad (2)$$

Reaction (1) is strongly pressure dependent and it will therefore be necessary to carry it out at a relatively high pressure in order to obtain a good degree of conversion.

The conversion of carbon oxides and hydrogen in the first step with formation of DME as the essential intermediate product proceeds according to reactions (1) and (2) and also the reaction $$2CH_3OH \rightleftharpoons CH_3OCH_3 + H_2O \qquad (3)$$

This conversion only exhibits a small pressure dependency and therefore is advantageous when it is desired to operate at relatively low pressures. The conversion via DME is furthermore advantageous in those cases where the synthesis gas used as starting material has a relatively high CO/H$_2$ mole ratio.

The first step of the process according to the invention as mentioned may be carried out at a pressure of 10–80 bar, preferably 30–60 bar, and at a temperature of 200°–300° C., preferably 240°–270° C. The pressure to employ in any given case will depend on a number of factors. Generally, it will be preferred to carry out the conversion at that pressure at which the synthesis gas is available. If, for instance, the synthesis gas has been obtained by gasification of coal, the pressure at present-day technique will be of the order of magnitude 30 bar. It can be expected, however, that future technique will render higher pressures possible, e.g. 70 bar or more. Even if increased pressure involves some increase of the degree of conversion, it will generally be preferred to operate at the gasification pressure because compression work is thereby saved. Also the temperature to choose will depend on the practical embodiment, thus primarily on whether the conversion is operated in an adiabatic or in a cooled reactor. When using an adiabatic reactor a higher outlet temperature and hence a lower degree of conversion must be accepted since the lower limit of the inlet temperature is determined by the activity of the catalyst employed. Alternatively, it is possible to employ a number of adiabatic reactors in series, the gas stream between the reactors being cooled, whereby it is possible to limit the total temperature increase. In case of large plants it is particularly preferable to employ a reactor with radial flow, whereby it is possible to achieve the lowest possible pressure drop. When using a cooled reactor it is possible to maintain the temperature in the entire reactor within a narrow temperature range and accordingly, it is possible to optimize the temperature with regard to the other process parameters. Any form of cooled reactor may hereby be employed. A particularly preferred cooled reactor, however, is a reactor containing catalyst-filled tubes surrounded by boiling water as coolant. By using such a reactor there will be a possibility of utilizing the heat liberated in the first step to generate steam.

As catalyst may be used known catalysts having activity for reactions (1), (2), and (3) at the temperature employed. Thus, it is possible to use a single composite catalyst having activity for all of these three recations; or two catalysts one of which has activity for reactions (1) and (2), and the other for reaction (3). Specific examples are the so-called methanol catalysts since several of these have activity for both reaction (1) and reaction (2); and the so-called acidic dehydration catalysts which catalyze reaction (3).

It has been found by laboratory experiments that for reactions (1) and (2) it is advantageous to use oxides of zinc and chromium, oxides of zinc and aluminum, oxides of copper, chromium and zinc, or oxides of copper and zinc and aluminum as catalyst. Such catalysts are known. The oxides mentioned may be composite or complex oxides where the two or three metals are chemically and/or physically combined in one oxidic structure.

For reaction (3) it has been found by laboratory experiments that alumina (Al$_2$O$_3$) or alumina-containing catalysts are suitable. One useful such catalyst is a combination of alumina, such as $\gamma$-alumina, with silica (SiO$_2$), and also certain zeolites are useful in this reaction.

The catalysts may be used in the form of a mixture of particles containing a catalyst having activity for reactions (1) and (2), and particles containing a catalyst having activity for reaction (3), or they may have the form of particles each of which contains both types of catalyst.

The second step in the process according to the invention is carried out at substantially the same pressure as that used in the first step.

The supply of heat necessary for carrying out the conversion in the second step can be provided in several ways. Thus the second step may for instance be carried out in a reactor containing heating elements heated by externally generated heat or, alternatively, known reactor versions designed for heat supply to the cold part of the reactor by indirect heat exchange with the raw product stream may be used.

The catalyst to use in the second step of the reaction may be any conventional catalyst for converting MeOH and/or DME into hydrocarbons, especially high octane gasoline. The catalyst to use should be one of those having selectivity for the hydrocarbon fraction or fractions desired in the end product. Such catalysts may be of the kind the selectivity for the hydrocarbon fraction or fractions desired in the end product. Such catalysts may be of the kind the selectivity of which is connected with its chemical composition and physical structure, especially its pore structure. As examples of catalysts of this type may be mentioned synthetic zeolites, a large number of forms thereof being known and some of them described in the U.S. patent specifications mentioned in the first part of the present specification, notably U.S. Pat. Nos. 3,702,886, 3,709,979, and 3,832,449.

In the following the process according to the invention will be further illustrated by some examples. The examples have been worked out on the basis of three pilot experiments, each having a duration of 500 hours.

EXAMPLE 1

A stream 1 of synthesis gas of 5.6 Nm$^3$/h and a recycle stream 11 of 25.0 Nm$^3$/h are jointly as feed stream 2 passed to cooled reactor 3 in which conversion to MeOH is carried out at a pressure of 60 bar and a temperature of 240° C.

An intermediate product stream 4 of 23.0 Nm$^3$/h is obtained and this is passed to second reactor 5 in which conversion to hydrocarbons is carried out at an inlet temperature of 330° C., heat being supplied by means of electrical heating elements to obtain an outlet temperature of 430° C.

Raw product stream 6 of 23.1 Nm$^3$/h is obtained and this is cooled to a temperature of 15° C. in separator 7 and is then separated into side stream 8 of 26.3 Nm$^3$/h, product stream 9 of 0.52 kg/h and side stream 10 of 1.2 kg/h (mainly consisting of water). The main part of side stream 8 is recycled as recycle stream 11 and the rest is conducted away as purge stream 12 of 1.3 Nm$^3$/h.

TABLE 1

| Stream | Gas compositions in mole % | | |
|---|---|---|---|
| | 1 | 2 | 11 |
| $H_2$ | 76.2 | 85.0 | 86.8 |
| CO | 15.3 | 3.2 | 0.6 |
| $CO_2$ | 7.2 | 1.9 | 0.9 |
| $CH_4$ | 0.6 | 5.7 | 6.7 |
| $C_2$ | 0.4 | 1.6 | 1.7 |
| $C_3$ | — | 1.4 | 1.7 |
| $C_4$ | — | 1.0 | 1.2 |
| $C_5$ | — | 0.3 | 0.3 |

EXAMPLE 2

Process as in Example 1, however, without heat supply to the reactor 5 and using an inlet temperature of 360° C. and an outlet temperature of 430° C.

The streams 1, 2, and 11 are of essentially the same composition as in Example 1.

EXAMPLE 3

Process as in Example 1, however, without heat supply to the reactor 5 and using an inlet temperature of 320° C. and an outlet temperature of 390° C.

The streams 1, 2, and 11 are of essentially the same composition as in Example 1.

In all three experiments a number of samples from the product stream 9 were collected for determining the product composition. Furthermore, a number of measurements of the temperature profile downwards through the reactor 5 were carried out to determine the deactivation rate of the catalyst. Knowing the change of the temperature profile per unit of time and also the geometry of the reactor the amount of catalyst deactivated per unit of time can be determined. Knowing furthermore the amount of MeOH converted per unit of time, it is possible to calculate the so-called resistance number R which expresses the amount (kg) of MeOH converted per amount (g) of catalyst deactivated.

The typical product compositions as well as the resistance numbers according to the Examples 1-3 are shown in the following Table 2.

TABLE 2

| Typical product composition and resistance number | | | |
|---|---|---|---|
| Example No. | Typical product composition, weight % | | Resistance number, kg/g |
| 1 | Durene | 4 | 15 |
| | Other $C_7$–$C_{10}$– aromatics | 36 | |
| | Other $C_5$+ | 60 | |
| 2 | Durene | 4 | 2,7 |
| | Other $C_7$–$C_{10}$– aromatics | 36 | |
| | Other $C_5$+ | 60 | |
| 3 | Durene | 17 | 12 |
| | Other $C_7$–$C_{10}$– aromatics | 40 | |
| | Other $C_5$+ | 43 | |

We claim:

1. In a process for the preparation of synthetic hydrocarbons by catalytic conversion of a synthesis gas containing hydrogen and carbon oxides, comprising (a) converting in a first step a feed stream containing the synthesis gas in the presence of a catalyst, at a pressure of 10–80 bar and a temperature of 200°–300° C. into an intermediate product containing methanol and/or dimethyl ether, and (b) converting in a second step the entire intermediate product from the first step, in the presence of a catalyst and at substantially the same pressure as in the first step, to form a raw product steam of hydrocarbons, cooling said raw product stream and thereby separating it into a a condensed product stream and a gaseous recycle stream, recycling said recycle stream without further separation to the inlet of the first step, the improvement of carrying out the second conversion step at an inlet temperature of 300°–340° C., while supplying heat to obtain an outlet temperature of 410°–440° C., the difference between inlet temperature and outlet temperature being at the same time at least 30° C. higher than the temperature increase caused by the heat generated by the chemical reaction taking place in the second step.

2. A process according to claim 1 wherein the inlet temperature employed in the second step is 320°–330° C. and the outlet temperature 420°–430° C.

3. A process according to claim 1 or 2 wherein the second step is carried out in a reactor in which heat is supplied by indirect heat exchange with the raw product stream, formed in that second conversion step.

* * * * *